US00PP17360P2

(12) United States Plant Patent
Saunders

(10) Patent No.: US PP17,360 P2
(45) Date of Patent: Jan. 16, 2007

(54) ***BUXUS SEMPERVIRENS* 'HIRAM SAUNDERS'**

(50) Latin Name: *Buxus sempervirens*
Varietal Denomination: Hiram Saunders

(75) Inventor: Hiram Wade Saunders, Albemarle, NC (US)

(73) Assignee: Plant Development Services Inc., Loxley, AL (US)

( * ) Notice: Subject to any disclaimer, the term of this patent is extended or adjusted under 35 U.S.C. 154(b) by 38 days.

(21) Appl. No.: 11/067,529

(22) Filed: Feb. 28, 2005

(51) Int. Cl.
*A01H 1/00* (2006.01)

(52) U.S. Cl. ..... Plt./226
(58) Field of Classification Search ..... Plt./226
See application file for complete search history.

(56) References Cited

PUBLICATIONS

Clemson Extension Home and Garden Information Center, "Boxwood", [online], retrieved on Oct. 1, 2005, retrieved from Internet http://hgic.clemson.edu/factsheets/GIC106.htm.*

Commercial Boxwood Production, Leaflet No. 407, Feb. 1997, [online], retrieved on Oct. 1, 2005, retrieved from the Internet http://www.ces.ncsu.edu/depts/hort/hil/hil–407.html.*

* cited by examiner

*Primary Examiner*—Anne Marie Grunberg
*Assistant Examiner*—Georgia Helmer

(57) ABSTRACT

A new and distinct variety of *Buxus sempervirens* plant which possesses a compact growth habit and attractive glossy evergreen foliage.

1 Drawing Sheet

Genus species: *Buxus sempervirens.*
Varietal denomination: 'Hiram Saunders'.

BACKGROUND OF THE INVENTION

The present invention relates to a new and distinct cultivar of *Buxus,* botanically known as *Buxus sempervirens,* and hereinafter referred to by the cultivar name 'Hiram Saunders'. This new *Buxus* variety was discovered by Hiram Wade Saunders in 1969 as a branch sport of an unnamed and unpatented single plant of *Buxus sempervirens* maintained at his home in Albemarle, N.C. The value of this new cultivar lies in its unique compact growth habit and attractive glossy evergreen foliage. 'Hiram Saunders' has retained many of the outstanding attributes of the species, in particular its tolerance of insects and diseases, which makes it adaptable to culture in the Sunbelt States.

Asexual propagation of the new plant by cuttings has been under Mr. Saunders' direction at the same location. The new plant retains its distinctive characteristics and reproduces true to the type in successive generations. The plant cannot be reproduced true from seed.

SUMMARY OF THE INVENTION

The following are the most outstanding and distinguishing characteristics of this new cultivar when grown under normal horticultural practices in Albemarle, N.C.

1. Low compact growth habit.
2. Attractive glossy evergreen foliage.
3. Easily propagated with semi-hardwood cuttings in late spring through the summer.
4. Tolerates full sun to part shade.
5. Tolerates heat and drought.

6. Relatively pest resistant.
7. Good specimen plant.
8. Desirable in planters.
9. Makes a very good low growing hedge or edge plant.
10. Tolerates pruning and shearing.
11. Hardy to Zone 5.

DESCRIPTION OF THE DRAWINGS

This new *Buxus sempervirens* variety is illustrated by the accompanying photographic prints in which:

1. The photograph at the top of the sheet is a close-up of the new variety, 'Hiram Saunders', showing the compact growth habit and glossy evergreen foliage.

2. The photograph at the bottom of the sheet shows the low compact growth habit of a young three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Buxus* based on my observations made of 10 year old plants grown in 7 gallon containers in wholesale commercial production practices, in greenhouses, and in established landscape plantings in Albemarle, N.C.

DISTINCTIVE CHARACTERISTICS

TABLE 1

| Characteristic | *Buxus s.* 'Hiram Saunders' | *Buxus s.* 'Suffruticosa' | *Buxus* hybrid 'Green Ice' pp#10,773 | *Buxus s.* The Species |
|---|---|---|---|---|
| Height (Mature) | 1–2' | 2–3' | 4' | 15–20' |
| Width (Mature) | 1–2' | 1–2' | 3' | 15–20' |
| Growth Habit | Very low compact | Low compact | Upright compact | Upright compact |
| Leaf Length | ½–⅞" | ⅓–¾" | ¾–1" | ½–1" |
| Leaf Width | ¼–7/16" | 3/16–⅜" | ¼–½" | ¼–½" |
| Leaf Shape | Elliptic-ovate | Elliptic-obovate | Lanceolate | Elliptic-lanceolate |
| Oblong Leaf Apex | Obtuse-acute | Obtuse-emarginate | Acuminate | Obtuse-emarginate |
| Growth Rate | Slow | Slow | Fast | Fast |
| Hardy Zone | 5 | 5 | 4 | 5 |

*Buxus hybrid* 'Green Ice' U.S. Plant Pat. No. 10,773, the non-patented variety *Buxus sempervirens* 'Suffruticosa', and the unnamed and non-patented species *Buxus sempervirens,* are well known in the industry and are comparable to 'Hiram Saunders', however, there are many differences.

In side-by-side comparisons conducted in Albemarle, N.C., 'Hiram Saunders' has a lower more compact growth habit, slower growth rate, and smaller leaves than *Buxus* hybrid 'Green Ice' and typical plants of the species *Buxus sempervirens.* 'Hiram Saunders' and *Buxus sempervirens* 'Suffruticosa' are both low compact growers with slow growth rates; however, in a period of 10 years 'Suffruticosa' matures to three feet and 'Hiram Saunders' matures to two feet. 'Hiram Saunders' also has a larger, more pointed leaf which is wider at the base than 'Suffruticosa'.

Classification:

Botanical: *Buxus sempervirens* 'Hiram Saunders'.

Parentage: Branch sport of a single plant of the species *Buxus sempervirens.*

Commercial: Broadleaf evergreen.

Form: Dense and rounded.

Height: 1–2'.

Width: 1–2'.

Growth habit: Very low, dense, and rounded.

Growth rate: Slow under normal fertilization and moisture conditions. Mature height is 1–2 feet and width is 1–2 feet. This varies from the parent which has a 15–20' mature height. Rooted cuttings can be produced in 4–5 months when propagated in late spring in Albemarle, N.C. Root development is vigorous and finely branched. From a rooted cutting, the new variety reaches a height of 10" and a spread of 10" in a period of four years. Under normal growing conditions in Albemarle, N.C., the growth rate is about 2–3" per year while maintaining a dense habit due to the abundant branch development and short internode lengths. The mature root system is fibrous and shallow.

Foliage: Opposite, simple, evergreen, non-fragrant, elliptic to ovate, ½" to ⅞" long and ¼" to 7/16" wide. Apex is obtuse to acute. The base is cuneate and the margin is entire. The petioles are 1/16" to ⅛" long, 1/32" in diameter, slightly pubescent and Yellow-Green Group 145B maturing to Yellow-Green Group 144B. Leaf venation is pinnate. Midribs are impressed on the upper surface (Yellow-Green Group 144D maturing to Yellow-Green Group 144C) and the primary lateral veins are obscure. Midribs are prominant on the underside (Yellow-Green Group 145C maturing to Yellow-Green Group 145B) and the lateral veins are obscure. The upper surface of the immature leaf is glossy, glabrous, and Yellow-Green Group 144A. The lower surface of the immature leaf is Yellow-Green Group 144B, matte and glabrous. The upper surface of the mature leaf is Green Group 137A, glossy, and glabrous and the underside is Yellow-Green Group 146C, matte and glabrous. With the onset of cool weather in the fall, the immature foliage color changes to Yellow-Green Group 152C on the upper surface and Yellow-Green Group 153A on the lower surface. At this point the midrib coloration is Yellow-Green Group 152D upper surface and Yellow-Green Group 153C lower surface. Mature foliage color is persistent through the winter.

In 1998, the date of initial spring growth was April 10, in Albemarle, N.C. After the initial spring flush there was almost continuous slow growth until fall, ending October 8, also in Albemarle, N.C. When grown in full sun, the internode length of this plant is ¼" to ⅜"; when grown in light shade the internode length is 5/16" to ½". As would be expected, a plant grown in the shade results in a taller, less dense plant with larger leaves.

Stems: The young shoots are Yellow-Green Group 145B, quadrangular, puberulent, and matte. In about four months they change to Yellow-Green Group 144B. Stems mature to Greyed-Orange Group 165C and after a year or so become rounded, glabrous, and rugose. Immature stem diameter is 1/16" and matures to ⅛". The plant is densely branched throughout the shrub. The pith is solid and uniform.

Buds:

*Flower.*—None have been observed to date.

*Vegetative.*—Small, solitary, sessile, conical, imbricate, Greyed-Orange Group 174A, ⅛" to 3/16" long and 1/16" wide.

Flowers: None have been observed to date.

Fruit: None have been observed to date.

Culture: Grows well in a wide range of conditions and tolerates full sun to part shade. Prefers a moist, well-drained soil that is rich in organic matter but is adaptable. Responds well to mulching and medium applications of fertilizer; prefers ph 5.0 to 6.5. Very little pruning is needed. Cold hardiness and drought resistance are comparable to the parent species. Propagated with semi-hardwood cuttings in late spring through the summer.

Disease and insect resistance: Resistance to disease and insects common to plants of *Boxwood* has not been observed.

I claim:

1. A new and distinct variety of *Buxus* plant named 'Hiram Saunders', as illustrated and described.

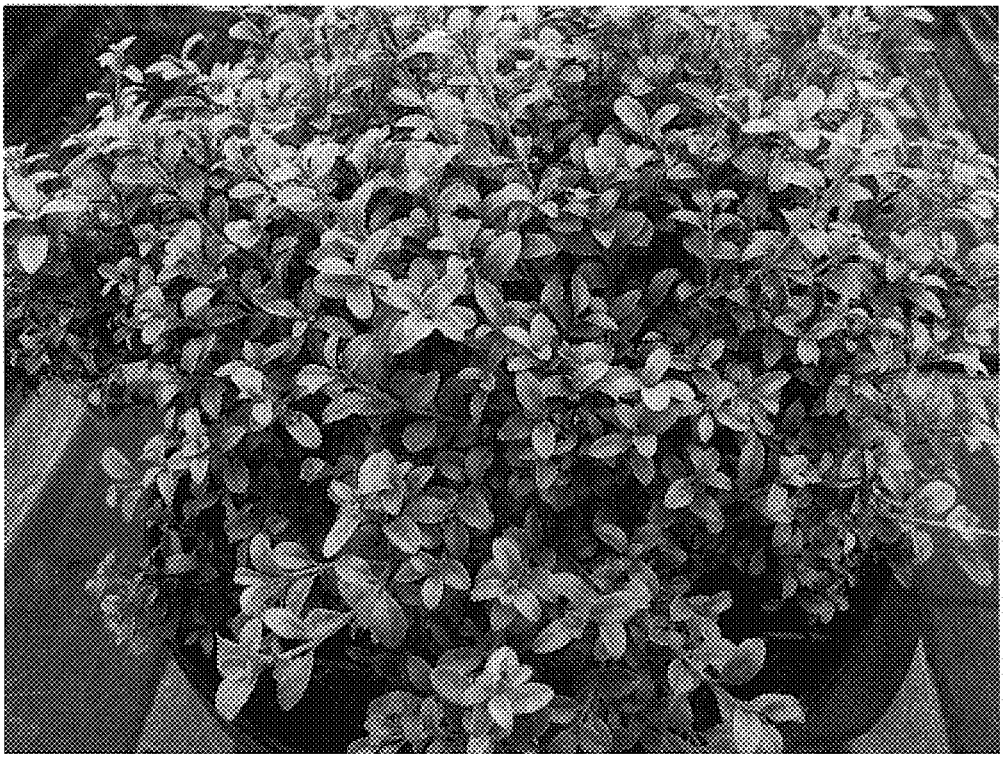
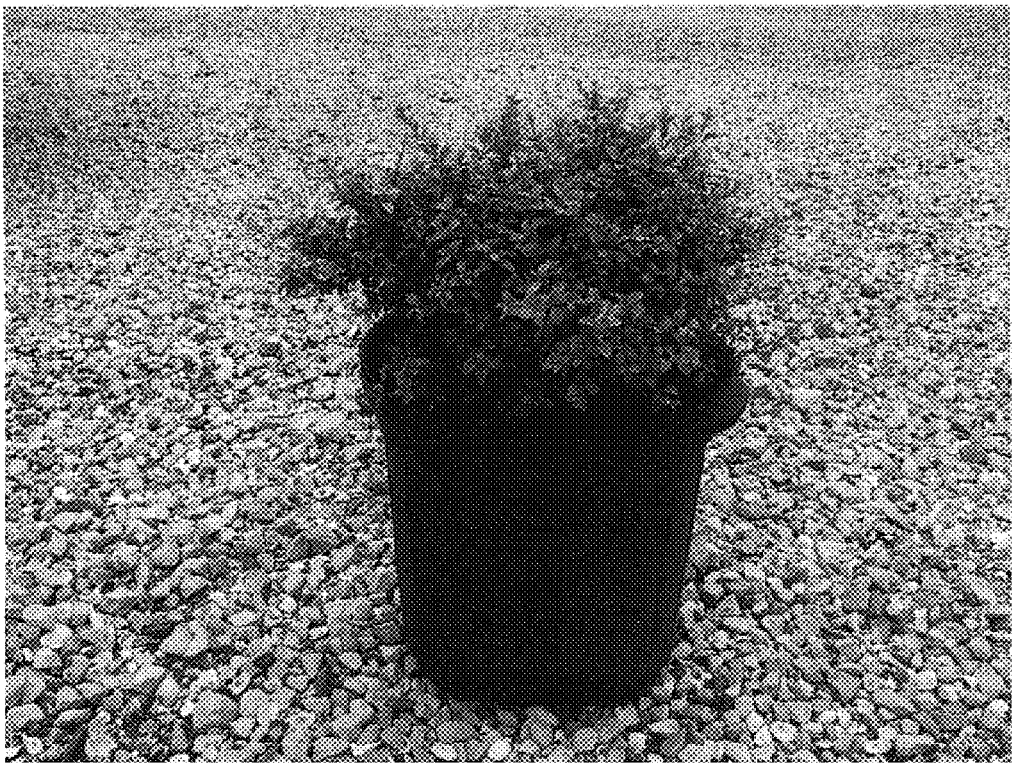

* * * * *